United States Patent
Yaron et al.

(10) Patent No.: US 6,558,342 B1
(45) Date of Patent: May 6, 2003

(54) FLOW CONTROL DEVICE, INTRODUCER AND METHOD OF IMPLANTING

(75) Inventors: Ira Yaron, Har Adar (IL); Orit Yarden, Givat Shmuel (IL)

(73) Assignee: Optonol Ltd., Neve Ilan (IL)

( * ) Notice: Subject to any disclaimer, the term of this patent is extended or adjusted under 35 U.S.C. 154(b) by 0 days.

(21) Appl. No.: 09/324,694

(22) Filed: Jun. 2, 1999

(51) Int. Cl.[7] .................................................. A61M 5/00
(52) U.S. Cl. ........................................ 604/9; 604/264
(58) Field of Search .............................. 606/108; 604/9, 604/93, 264, 8, 10, 30, 523, 164.01, 164.02, 164.04

(56) References Cited

U.S. PATENT DOCUMENTS

| 15,192 | A | 6/1856 | Peale | |
|---|---|---|---|---|
| 274,447 | A | 3/1883 | Kennish | |
| 733,152 | A | 7/1903 | Chisholm | |
| 1,388,172 | A | 8/1921 | Craddock | |
| 2,431,587 | A | 11/1947 | Schnee | 128/348 |
| 2,555,076 | A | 5/1951 | Crossley | 128/303 |
| 2,867,213 | A | 6/1959 | Thomas, Jr. | 128/350 |
| 3,159,161 | A | 12/1964 | Ness | 128/350 |
| 3,310,051 | A | 3/1967 | Schulte | 128/216 |
| 3,333,588 | A | 8/1967 | Schulte | 128/350 |

(List continued on next page.)

FOREIGN PATENT DOCUMENTS

| EP | 102747 A | 3/1984 |
|---|---|---|
| EP | 228185 A | 7/1987 |
| FR | 2 757 068 | 6/1998 |
| JP | 8-155540 | 6/1996 |
| RU | 1191227 | 11/1985 |
| SU | 1797884 | 2/1993 |
| WO | WO93/20783 | 10/1993 |
| WO | WO94/02081 | 2/1994 |
| WO | WO94/09837 | 5/1994 |
| WO | WO94/13234 | 6/1994 |
| WO | WO94/17755 | 8/1994 |

(List continued on next page.)

OTHER PUBLICATIONS

Prata, Jr., et al., "In Vitro an In Vivo Flow Characteristics of Glaucoma Drainage Implants," Ophthalmology, vol. 102, No. 5, Jun. 1995.

Krupin et al., "Draiange Implants," Glaucoma, edited by Kaufman et al., Section VII, 1994.

Sidoti et al., "Glaucoma Drainage Implants," Current Opinion in Ophthalmology, 1994.

Middleton & Tipton, "Synthetic Biodegradable Polymers as Medical Devices," Medical Products and Biomaterials, 1998.

*Primary Examiner*—Sharon Kennedy
(74) *Attorney, Agent, or Firm*—Kenyon & Kenyon

(57) ABSTRACT

An implant having a tube for permitting fluid flow has an outer flange at the outlet end and a retention projection near the inlet end. A delivery device for implanting the implant has a central bore for accommodating the implant during the implantation procedure. When the implant is loaded in the delivery device, the retention projection of the implant protrudes beyond the outside surface of the delivery device. After the delivery device and implant have penetrated the tissue through which drainage is desired, and the retention projection has fully penetrated through the tissue, the delivery device is withdrawn. The retention projection acts as a hook engaging the inside surface of the tissue, causing the implant to stay implanted in the tissue. An implant may also be provided with a mechanism for temporary occlusion, in whole or in part, of the flow passage. Thus, the tube passage may be filled, partially or wholly, with absorbable material and/or a plurality of withdrawable or advanceable flow controlling strands.

14 Claims, 4 Drawing Sheets

U.S. PATENT DOCUMENTS

| | | | |
|---|---|---|---|
| 3,421,509 A | 1/1969 | Fiore | 128/349 |
| 3,530,860 A | 9/1970 | Majoros | 606/109 |
| 3,788,327 A | 1/1974 | Donowitz et al. | 128/350 R |
| 3,884,238 A | 5/1975 | O'Malley et al. | 128/305 |
| 3,890,976 A | 6/1975 | Bazell et al. | 128/351 |
| 3,913,584 A | 10/1975 | Walchle et al. | 606/109 |
| 3,915,172 A | 10/1975 | Wichterle et al. | 128/350 |
| 3,938,529 A | 2/1976 | Gibbons | 128/349 |
| 3,957,035 A | 5/1976 | Chassaing | 128/2 T |
| 3,976,077 A | 8/1976 | Kerfoot, Jr. | 128/305 |
| 4,037,604 A | 7/1977 | Newkirk | 128/350 |
| 4,175,563 A | 11/1979 | Arenberg et al. | 128/350 V |
| 4,299,227 A | 11/1981 | Lincoff | 128/344 |
| 4,402,681 A | 9/1983 | Haas et al. | 604/9 |
| 4,457,757 A | 7/1984 | Molteno | 604/294 |
| 4,474,569 A | 10/1984 | Newkirk | 604/8 |
| 4,521,210 A | 6/1985 | Wong | 604/8 |
| 4,538,611 A | 9/1985 | Kelman | 128/305 |
| 4,554,918 A | 11/1985 | White | 604/10 |
| 4,563,779 A | 1/1986 | Kelman | 623/5 |
| 4,578,058 A | 3/1986 | Grandon | 604/27 |
| 4,587,954 A | 5/1986 | Haber | 128/1 R |
| 4,598,705 A | 7/1986 | Lichtenberger | 128/200.26 |
| 4,604,087 A | 8/1986 | Joseph | 604/9 |
| 4,634,418 A | 1/1987 | Binder | 604/8 |
| 4,645,493 A | 2/1987 | Ferrando et al. | 604/174 |
| 4,692,142 A | 9/1987 | Dignam et al. | 604/51 |
| 4,722,724 A | 2/1988 | Schocket | 604/8 |
| 4,750,901 A | 6/1988 | Molteno | 604/8 |
| 4,751,926 A | 6/1988 | Sasaki | 128/303 |
| 4,781,675 A | 11/1988 | White | 604/10 |
| 4,787,885 A | 11/1988 | Binder | 604/8 |
| 4,808,183 A | 2/1989 | Panje | 623/9 |
| 4,813,941 A | 3/1989 | Shea | 604/247 |
| 4,826,478 A | 5/1989 | Schocket | 604/8 |
| 4,886,488 A | 12/1989 | White | 604/9 |
| 4,909,783 A | 3/1990 | Morrison | 604/30 |
| 4,934,363 A | 6/1990 | Smith et al. | 606/107 |
| 4,936,825 A | 6/1990 | Ungerleider | 604/8 |
| 4,946,436 A | 8/1990 | Smith | 604/8 |
| 4,964,850 A | 10/1990 | Bouton et al. | 604/54 |
| 4,968,296 A | 11/1990 | Ritch et al. | 604/8.11 |
| 5,000,731 A | 3/1991 | Wong | 604/8 |
| 5,041,081 A | 8/1991 | Odrich | 604/9 |
| 5,053,040 A | 10/1991 | Goldsmith, III | 606/109 |
| 5,064,417 A | 11/1991 | Andreussi | 604/175 |
| 5,071,408 A | 12/1991 | Ahmed | 606/108 |
| 5,073,163 A | 12/1991 | Lippman | 604/9 |
| 5,092,837 A | 3/1992 | Ritch et al. | 604/8 |
| 5,098,393 A | 3/1992 | Amplatz et al. | 604/167 |
| 5,098,438 A | 3/1992 | Siepser | 606/107 |
| 5,106,367 A | 4/1992 | Ureche et al. | 604/30 |
| 5,127,901 A | 7/1992 | Odrich | 604/9 |
| 5,139,502 A | 8/1992 | Berg et al. | 606/108 |
| 5,147,370 A | 9/1992 | McNamara et al. | 606/108 |
| 5,167,620 A | 12/1992 | Ureche et al. | 604/28 |
| 5,171,213 A | 12/1992 | Price, Jr. | 604/8 |
| 5,178,604 A | 1/1993 | Baerveldt et al. | 604/8 |
| 5,190,552 A | 3/1993 | Kelman | 606/107 |
| 5,207,660 A | 5/1993 | Lincoff | 604/300 |
| 5,221,278 A | 6/1993 | Linkwitz et al. | 604/890 |
| 5,242,449 A | 9/1993 | Zaleski | 606/107 |
| 5,300,020 A | 4/1994 | L'Esperance, Jr. | 604/9 |
| 5,318,558 A | 6/1994 | Linkwitz et al. | 604/892 |
| 5,322,504 A | 6/1994 | Doherty et al. | 606/167 |
| 5,326,345 A | 7/1994 | Price, Jr. | 623/4 |
| 5,338,291 A | 8/1994 | Speckman et al. | 604/9 |
| 5,342,370 A | 8/1994 | Simon et al. | 606/107 |
| 5,346,464 A | 9/1994 | Camras | 604/9 |
| 5,358,492 A | 10/1994 | Feibus | |
| 5,360,398 A | 11/1994 | Grieshaber et al. | 604/30 |
| 5,360,399 A | 11/1994 | Stegmann | 604/49 |
| 5,370,607 A | 12/1994 | Memmen | 604/8 |
| 5,372,577 A | 12/1994 | Ungerleider | 604/8 |
| 5,380,290 A | 1/1995 | Makower et al. | 604/164 |
| D356,867 S | 3/1995 | Krupin | D24/155 |
| 5,397,300 A | 3/1995 | Baerveldt et al. | 604/8 |
| 5,403,323 A | 4/1995 | Smith | 606/107 |
| RE34,998 E | 7/1995 | Langerman | 623/6 |
| 5,433,701 A | 7/1995 | Rubinstein | 604/8 |
| 5,433,714 A | 7/1995 | Bloomberg | 604/289 |
| 5,451,229 A | 9/1995 | Geuder et al. | 606/107 |
| 5,454,796 A | 10/1995 | Krupin | 604/294 |
| 5,476,445 A | 12/1995 | Baerveldt et al. | 604/8 |
| 5,494,484 A | 2/1996 | Feingold | 606/107 |
| 5,520,631 A | 5/1996 | Nordquist et al. | 604/8 |
| 5,522,845 A | 6/1996 | Wenstom, Jr. | 606/78 X |
| 5,558,629 A | 9/1996 | Baerveldt et al. | 609/8 |
| 5,558,630 A | 9/1996 | Fisher | 604/8 |
| 5,626,559 A | 5/1997 | Solomon | 604/9 |
| 5,702,414 A | 12/1997 | Richter et al. | 606/166 |
| 5,709,698 A | 1/1998 | Adams et al. | 606/180 |
| 5,713,844 A | 2/1998 | Peyman | 604/9 |
| 5,720,760 A | 2/1998 | Becker et al. | 606/180 |
| 5,800,376 A | 9/1998 | Watson et al. | |
| 5,807,240 A | 9/1998 | Muller et al. | 600/135 |
| 5,868,697 A | 2/1999 | Richter et al. | 604/8 |
| 5,968,058 A | 10/1999 | Richter et al. | 606/166 |
| 6,186,974 B1 | 2/2001 | Allan et al. | 604/30 |
| 6,203,513 B1 | 3/2001 | Yaron et al. | 604/9 |

FOREIGN PATENT DOCUMENTS

| | | |
|---|---|---|
| WO | WO94/21443 | 9/1994 |
| WO | WO95/35078 | 12/1995 |
| WO | WO96/03944 | 2/1996 |
| WO | WO96/20742 | 7/1996 |
| WO | WO96/36377 | 11/1996 |
| WO | WO 98/30181 | 1/1998 |
| WO | WO 99/26567 | 6/1999 |

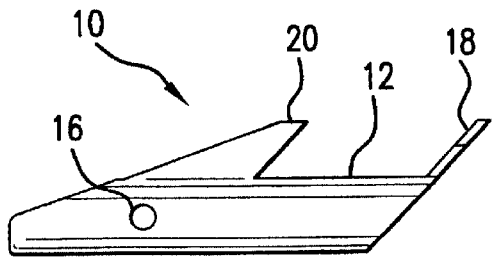 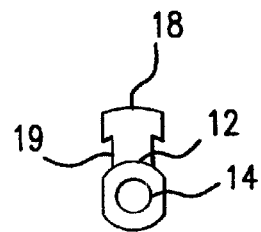
FIG.1A  FIG.1B
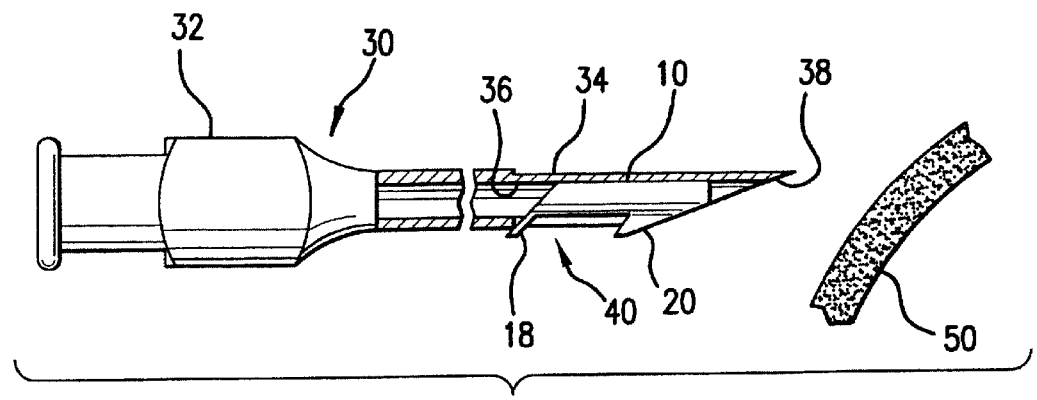
FIG.2A
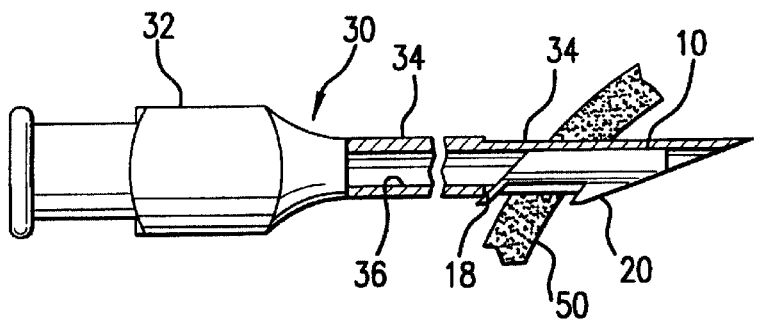
FIG.2B
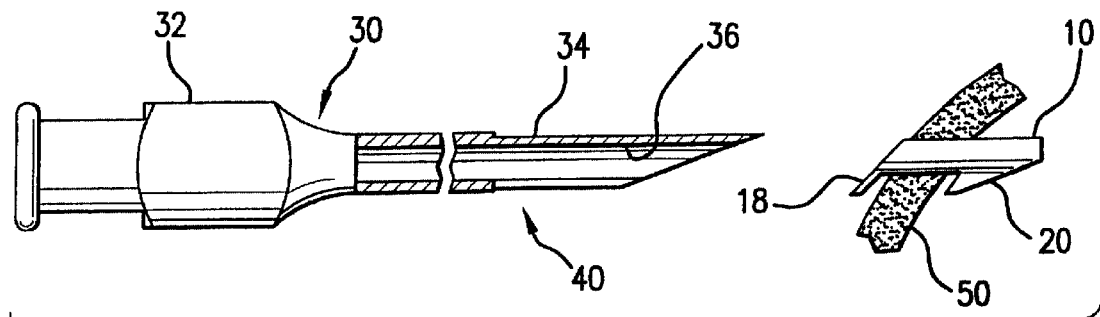
FIG.2C

FLOW CONTROL DEVICE, INTRODUCER AND METHOD OF IMPLANTING

FIELD OF THE INVENTION

The invention relates generally to medical implants used to regulate the flow of fluids within the body. The invention may be applied, for example, to ophthalmic implants for treatment of glaucoma. The invention also relates to delivery devices for implanting such implants, to methods of implanting such implants, and to methods of manufacturing such implants.

BACKGROUND OF THE INVENTION

Medical implants used to regulate the flow of fluids within the human body are known and used. One application for the use of such implants is in the treatment of glaucoma. Typical ophthalmic implants utilize drainage tubes for the release of aqueous humor from the eye to relieve the intraocular pressure (IOP).

Several disadvantages have at times been associated with prior implants. For example, implants using valve mechanisms to regulate fluid flow have risked malfunction due to defects in and/or failure of such valve mechanisms. Depending on such factors as the site of implantation, some implants have tended to clog while in use due to tissue covering the inlet end or the outlet end of the drainage tube. In addition, prior implants at times have required insertion operations that are complicated, costly, and time-consuming, for example requiring suturing of the implant once it is in place.

PATENTS AND APPLICATIONS INCORPORATED BY REFERENCE

The assignee of this patent application is also the assignee of other patents and patent applications describing and illustrating implants directed at overcoming some of the drawbacks associated with prior implants, as well as delivery devices for such implants, methods of using such implants, and methods of manufacturing such implants.

For example, implants, delivery devices, methods of use, and methods of manufacturing are described and illustrated in U.S. Pat. Nos. 5,868,697 and 5,702,414, both of which are owned by the assignee of this application, and both of which are hereby expressly incorporated by reference into this application.

Further examples of such implants, delivery devices, methods of use, and methods of manufacturing are also described and illustrated, in U.S. Pat. No. 6,203,513 filed Nov. 20, 1997, which is also owned by the assignee of this application, and which is also hereby expressly incorporated by reference into this application.

SUMMARY OF THE INVENTION

One object of the invention is to provide a flow regulating implant and an associated delivery device that enable the implant to be inserted in a relatively simple and efficient procedure.

In one embodiment in accordance with the invention, an implant having a tube for permitting fluid flow has an outer flange at the outlet end and one or more retention projections near the inlet end. An introducer or delivery device for implanting the implant has a central bore for accommodating the implant during the implantation procedure. The implant and delivery device are designed so that when the implant is loaded in the delivery device, the retention projection or projections of the implant protrude from the delivery device to act as a hook or hooks during the procedure.

In accordance with a method of using the implant and delivery device according to an embodiment of the invention, the implant is loaded in the delivery device with the retention projection protruding from the delivery device. The delivery device and implant then penetrate the tissue through which drainage is desired, for example, the sclera of an eye. Once the retention projection has fully penetrated through the tissue, the delivery device is withdrawn. The retention projection acts as a hook engaging the inside surface of the tissue, causing the implant to stay implanted in the tissue when the delivery device is withdrawn.

The retention projection may be made, for example, of an elastic material, so that it is able to be flexed inward against the tube of the implant during penetration through the tissue. Alternatively, the retention projection may be designed to lie initially relatively flat against the tube for easier penetration and to prevent tearing of the tissue, with a mechanism for extending the retention projection outwardly when the implant is implanted.

Another object of the invention is to provide a simple and efficient method of manufacturing a flow regulating implant. In a method for manufacturing an implant according to an embodiment of the invention, the device may be molded out of a suitable material, for example, silicone. To provide the tube passage of the implant, a thin wire may be used during the molding process. The implant alternatively may be constructed out of stainless steel or any other suitable material.

A further object of the invention is to provide a flow regulating implant with beneficial flow characteristics. Thus, the implant may have various mechanisms for changing the configuration of the flow path. For example, a flow controlling rod or other obstruction may be placed in the tube passage for changing the dimensions within the tube passage. This rod or obstruction may be temporary. For example, it may be made of absorbable (biodegradable) material that is eroded and absorbed. Alternatively, it may be constructed in such a way that it may be removed from the tube passage or advanced into the tube passage at a period of time after implantation. For example, one or more strands, such as sutures, may be placed in the tube passage and withdrawn or advanced by a physician as desired at a later time or times.

An implant according to the invention has other applications aside from the field of intraocular implants. For example, the implant may be used for drainage of a hydrocele sac, regulating flow between the hydrocele sac and the subcutaneous scrotum. Persons of ordinary skill in the art will appreciate that other applications of an implant in accordance with the invention are possible, as are various modifications of the embodiments described herein, without departing from the scope of the invention as defined in the claims.

BRIEF DESCRIPTION OF THE DRAWINGS

FIG. 1A is a side view of a first embodiment of a drainage implant;

FIG. 1B is an end view of the drainage implant shown in FIG. 1A;

FIGS. 2A through 2C illustrate a delivery device and insertion of the drainage implant of FIG. 1A into desired tissue, with FIG. 2A showing the delivery device and implant before insertion, FIG. 2B showing the delivery device and implant being placed through the tissue, and FIG. 2C showing the inserted implant after the delivery device has been withdrawn;

DETAILED DESCRIPTION OF EMBODIMENTS OF THE INVENTION

Figure 3A:
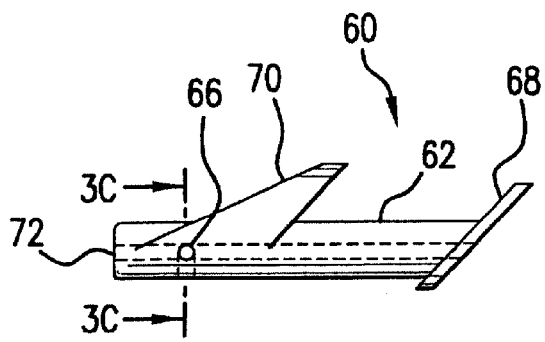
FIG. 3A is a side view of a second embodiment of a drainage implant.

FIGS. 1A and 1B show a side view and end view, respectively, of a first embodiment of a drainage implant 10 in accordance with the invention. The implant 10 has a tube 12 having a tube passage 14 for permitting fluid flow between an inlet end of the implant and an outlet end of the implant. One or more side holes 16 may be provided around the circumference of the tube 12 near the inlet end, allowing access for fluid flow into the tube passage 14.

The implant 10 has an outer flange 18 at the outlet end and a retention projection 20 near the inlet end. The plane of the outer flange 18 may form an angle with the tube 12, with the angle selected to correspond to the angle between the surface of the tissue into which the implant 10 is to be inserted and the axis of insertion of the tube 12 of the implant 10.

FIGS. 2A through 2C illustrate an introducer or delivery device 30 for implanting the implant 10 and the method of implanting the implant 10 with that delivery device 30. The delivery device 30 has handle 32 and a tube 34 having a central bore 36 for accommodating the implant 10 during the implantation procedure. The delivery device 30 has a beveled tip 38 to allow penetration of the tissue 50 into which the implant is to be inserted. In an alternative embodiment, the implant itself penetrates the tissue by its beveled tip at the inlet end.

An opening 40 is provided in the wall of the tube 34 of the delivery device 30. In this illustrated embodiment, the opening 40 allows both the retention projection 20 and the outer flange 18 to protrude beyond the wall of the tube 34 when the implant 10 is loaded in the delivery device 30. Because it projects beyond the wall of the tube 34, the retention projection 20 of the implant 10 can act as a hook during the implantation procedure.

As can be seen in FIG. 1B, the flange 18 of the implant 10 has notches or grooves 19 on either side. These notches or grooves 19 correspond approximately to the width of the wall of the tube 34 of the delivery device 30 and accommodate the wall of the tube 34 of the delivery device 30 when the implant 10 is loaded in the delivery device 30. The notches or grooves 19 may take any suitable shape. Alternatively, the flange 18 may have a continuous width, with no notches or grooves, with the width of the flange 18 being slightly narrower than the diameter of the tube 12 of the implant 10. Further variations of the configuration of the flange 18 are possible.

To use the implant 10 and delivery device 30, the implant 10 is loaded in the delivery device 30 with the retention projection 20 protruding from the delivery device, as shown in FIG. 2A. The delivery device 30, with the implant loaded inside, is then pressed through the tissue 50 through which drainage is desired, for example, the sclera of an eye. FIG. 2B illustrates the delivery device 30 pressed through the tissue 50.

To facilitate introduction of the delivery device 30 and/or implant 10 into the tissue 50, the delivery device 30 may be oriented such that the beveled tip 38 forms a sharper angle with the tissue 50. Thus, for example, the delivery device as shown in FIG. 2A may be rotated 180 degrees, i.e., with the retention projection 20 facing upward. In the case of an implant 10 being placed into the limbal sclera of an eye, this corresponds to the retention projection 20 being on the opposite side of the tube 12 from the iris. When the delivery device 30 and implant 10 are suitably through the tissue 50, they may be rotated to align the implant 10 properly in the tissue 50, with the flange 18 and retention projection 20 oriented as desired with respect to the tissue 50.

Once the retention projection 20 has fully penetrated through the tissue 50, the delivery device 30 is withdrawn. The retention projection 20 acts as a hook engaging the inside surface of the tissue 50, causing the implant 10 to stay implanted in the tissue 50 when the delivery device 30 is withdrawn. FIG. 2C illustrates the implant 10 implanted in the tissue 50, with the delivery device 30 withdrawn.

Since the tube 34 of the delivery device 30 is hollow, it may be used to inject fluid or viscoelastic material. Thus, fluid may be injected into the anterior chamber of an eye upon implantation to reduce the risk of hypotony. Similarly, a viscoelastic material may be injected under the conjunctiva to help fill the bleb that exists after implantation.

The implant 10 may be molded out of a suitable material, for example, silicone. To provide the tube passage 14 of the implant 10, a thin wire may be used during the molding process. More than one wire may be used, in order to have more than one tube passage in the implant. The implant alternatively may be constructed out of stainless steel or another suitable material. It may be coated with a suitable anti-fibrosis material, such as heparin.

The retention projection 20 may be formed of the same material as the rest of the implant 10. Alternatively, it may be made of a more flexible material to allow it to be flexed inward against the tube 12 of the implant 10 during penetration through the tissue 50. Alternatively, the retention projection 20 may be designed to lie initially relatively flat against the tube 12 for easier penetration and to prevent tearing of the tissue 50, to be extended outwardly by an expansion mechanism, for example a balloon, when the implant 10 is implanted.

Figure 3B:
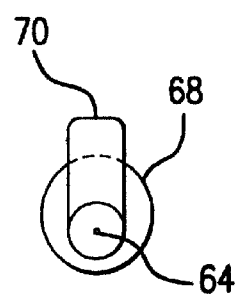
FIG. 3B is an end view of the drainage implant shown in FIG. 3A.
Figure 3C:
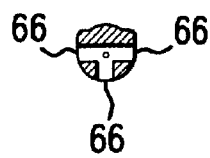
FIG. 3C is a cross-sectional view taken along the plane identified by the line 3C—3C in FIG. 3A.

FIGS. 3A, 3B and 3C show a side view, end view, and cross-section, respectively, of a second embodiment of a drainage implant 60 in accordance with the invention. Like the implant 10 shown in FIGS. 1A and 1B, the implant 60 in FIGS. 3A, 3B, and 3C has a tube 62 having a tube passage 64 and side holes 66 opening into the tube passage 64. The implant 60 also has an outer flange 68 at the outlet end and a retention projection 70 near the inlet end. In this case, the outer flange 68 projects beyond the outer surface of the tube 62 in all directions around the circumference of the tube 62.

Figure 4A:
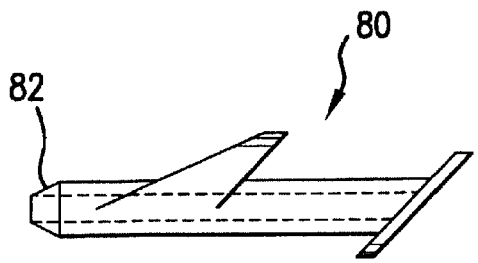
FIG. 4A is a side view of a third embodiment of a drainage implant.
Figure 4B:
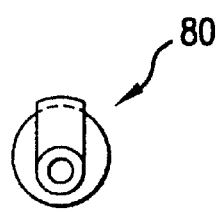
FIG. 4B is an end view of the drainage implant shown in FIG. 4A.

FIGS. 4A and 4B show a side view and end view, respectively, of a third embodiment of a drainage implant 80, similar to the implant 60 shown in FIGS. 3A, 3B, and 3C. The tip 82 of the implant 80 is conical, in contrast to the blunt tip 72 of the implant 60.

In an alternative construction, the implant may be made with a closed end with a slit in it. Fluid can only pass through the device when the pressure rises sufficiently to open the slit. Alternatively, a different portion along the length of the tube passage may be provided with such a construction.

Figure 5:
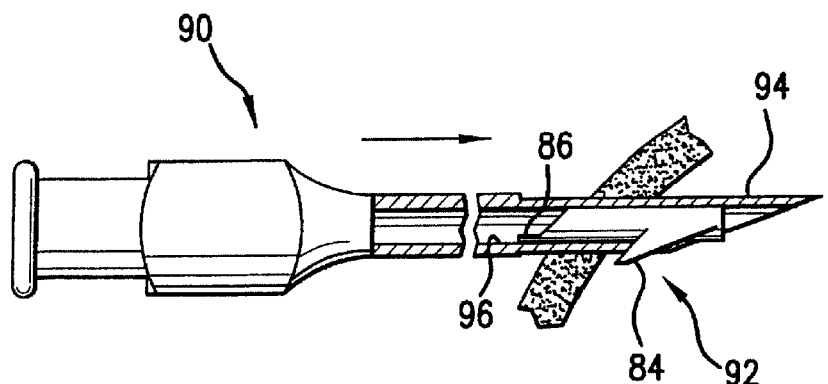
FIG. 5 illustrates a second embodiment of a delivery device with an implant inserted in the delivery device and with the procedure at a stage corresponding to that in FIG. 2B.

FIG. 5 illustrates an alternative embodiment of a delivery device 90 in accordance with the invention. In this embodiment, the opening 92 allows only the retention projection 84 of the implant to protrude beyond the wall of the tube 94 of the delivery device. The outer flange 86 is accommodated within the central bore 96 of the delivery device 90. In this embodiment, the outer flange 86 must be folded or bent to be accommodated within the central bore 96 of the delivery device 90. The outer flange 86 is resilient, so that when the implant is removed from the delivery device, the outer flange 86 extends to a position relatively coplanar with the outer surface of the tissue into which the implant is inserted.

Similarly, the retention projection 84 may also be constructed to be sufficiently resilient to allow it to be compressed and completely accommodated within the central bore 96 of the delivery device 90. In addition, the delivery device 90 may be constructed with the tube 94 having a continuous outer wall, with no opening 92. To facilitate removal of the implant from the delivery device, a pusher rod or wire may be located within the bore of the delivery device. By advancing the pusher rod or wire within the delivery device against the implant, the physician can force the implant out of the delivery device, thereby allowing the retention projection to expand outwardly to its initial, relaxed position, enabling it to engage the inside surface of the tissue.

Various mechanisms may be used, if desired, for giving different flow characteristics to the implant. It may be desirable to use implants with different flow characteristics for different patients and/or to have an implant in which the flow characteristics may be changed after implantation in a particular patient.

U.S. patent application Ser. No. 08/975,386, filed Nov. 20, 1997 and incorporated by reference herein, describes and illustrates various mechanisms for assisting in controlling the flow of fluid, e.g. aqueous humor, through an implant. It describes and illustrates the use of a flow controlling wire or rod in the tube passage of an implant.

The effect of the flow controlling rod or wire is to reduce the cross-sectional area through which the fluid flows for a particular length inside the tube passage of the implant. Because the flow is a function of the cross-section and length of the lumen through which it passes, the interposition of the flow controlling rod or wire serves to increase the resistance to flow. In an intraocular implant, for example, this assists in reducing the risk of hypotony.

The configuration and dimensions of the flow controlling rod or wire may be selected in accordance with the flow characteristics that are desired. It may have one or more internal bores or external grooves, any of which may be helically arranged to increase its length. It may be adjustable, by moving it axially or rotating it, to modify the flow characteristics. Persons skilled in the art will appreciate that numerous other variations are possible for the configuration of the flow controlling rod or wire.

The flow controlling rod or wire may have its axis aligned parallel with the axis of the tube passage, but other orientations are possible. For example, a flow controlling rod or wire having a diameter slightly smaller that the tube passage may be oriented transverse to the tube passage. The transversely oriented rod or wire will have a short length, corresponding approximately to the diameter of the tube or tube passage. It serves as an obstruction to the flow through the tube passage, altering the flow characteristics. Other obstruction may be placed in the tube passage for achieving similar results.

Another mechanism described and illustrated in U.S. patent application Ser. No. 08/975,386 for assisting in controlling the flow of fluid through an implant is the use of temporary occlusion. By occluding the flow passage of the implant with an absorbable material or with a material that may be removed after implantation, for example by a tool or laser probe, the resistance to flow can be reduced after implantation.

The use of temporary occlusion is advantageous in situations in which flow through the implant is desired to be kept low at implantation, and possibly also for a period of time after implantation. For example, when an implant is implanted in the eye, the incision in the conjunctiva and/or possible tearing of the sclera around the implant provide potential flow passages for aqueous humor. Thus, to reduce the risk of hypotony, it may be desirable to prevent or reduce flow through the implant upon.implantation and for a period thereafter. Once the conjunctiva and/or sclera have healed, the flow through the implant can be increased.

Figure 6:
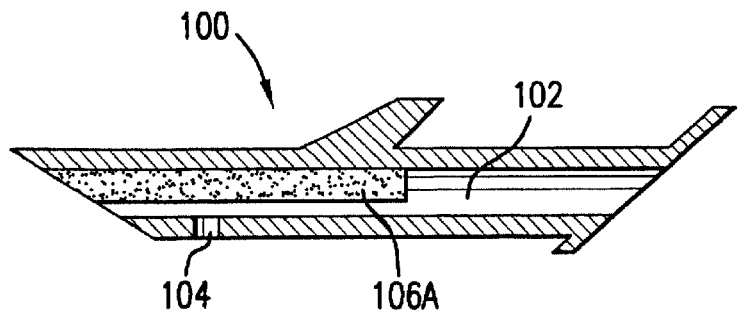
FIG. 6 illustrates an intraocular implant according to the invention with a flow controlling plug made of absorbable material in the tube passage.
Figure 7A:
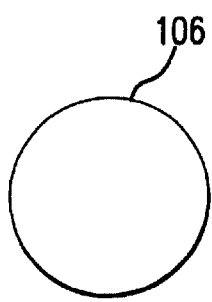
FIGS. 7A through 7D illustrate four variations of cross-sections for a flow controlling plug.
Figure 7B:
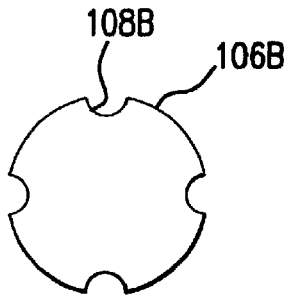
Figure 7C:
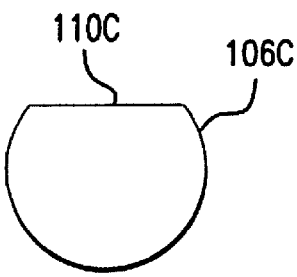
Figure 7D:
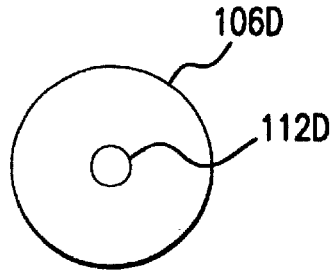

The temporary occlusion need not be limited to any particular part of the flow passage. For example, the side holes and/or the tube passage of the implant may be filled, partially or wholly, with absorbable material. Thus, for example, as shown in FIG. 6, a plug 106A of absorbable material may be placed in the tube passage 102 of the implant 100. With an absorbable material that biodegrades by surface erosion, as fluid contacts and flows adjacent to the plug 106A, the material of the plug 106A is absorbed into the fluid, thereby reducing the dimensions of the plug 106A. As the dimensions of the plug 106A are reduced, the resistance to flow through the implant is similarly reduced. Alternatively, an absorbable material that biodegrades by bulk erosion may be used. Absorbable (biodegradable) materials are known and used, and such materials are described, for example, in Middleton & Tipton, "Synthetic Biodegradable Polymers as Medical Devices," Medical Products and Biomaterials, March 1998.

FIG. 6 shows the plug 106A only partially filling the tube passage 102, but it will be appreciated that the plug 106A may completely fill the tube passage 106A. In that case, fluid flow would initially be completely obstructed. Fluid flow begins only after the plug 106A has been sufficiently absorbed to provide a path for fluid to flow out of the implant.

An absorbable plug may be used with any suitable configuration of implant, including implants with flow controlling rods or other flow controlling obstructions. Similarly, an absorbable plug may have any suitable configuration and dimensions, selected in accordance with the flow characteristics that are desired. If desired, more than one absorbable plug may be used.

Some possible cross-sectional shapes for alternative absorbable plugs are shown in FIGS. 7A through 7D. Absorbable plug 106A has a circular cross-section. Absorbable plug 106B is similar to absorbable plug 106A with the addition of external grooves 108B. Absorbable plug 106C has a flat surface 11OC. Absorbable plug 106D has a longitudinal bore 112D. Alternative constructions include combining external grooves and internal bores, changing the number of them, and/or arranging them helically or in any other suitable configuration. The absorbable plug may be in a tapered or other suitable shape. It will be appreciated that the configuration of the absorbable plug will affect the absorption of the absorbable plug, with the areas in contact with the fluid being absorbed first.

Figure 8:
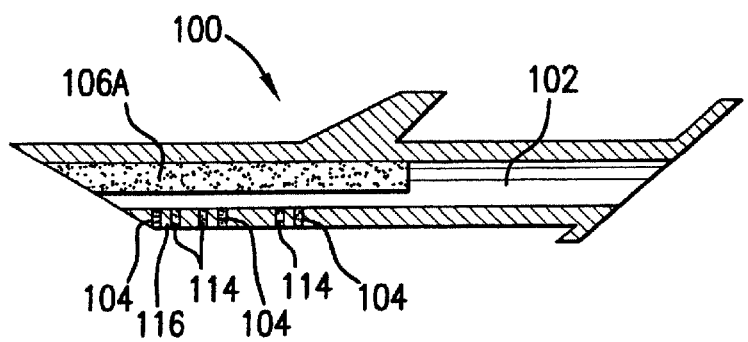
FIG. 8 illustrates an intraocular implant according to the invention with a flow controlling plug made of absorbable material in the tube passage and with side holes partially occluded by plugs made of absorbable material.

FIG. 8 shows the use of an absorbable plug 106A in conjunction with partially occluded side holes 104. Each of the side holes 104 is partially occluded by absorbable plugs 114, each of which has a central bore 116. As with the absorbable plug 106A in the tube passage 102, the absorbable plugs 114 in the side holes 104 may have any suitable configuration, and may be used in conjunction with any configuration of absorbable plug in the tube passage or with no absorbable plug in the tube passage.

Figure 9:
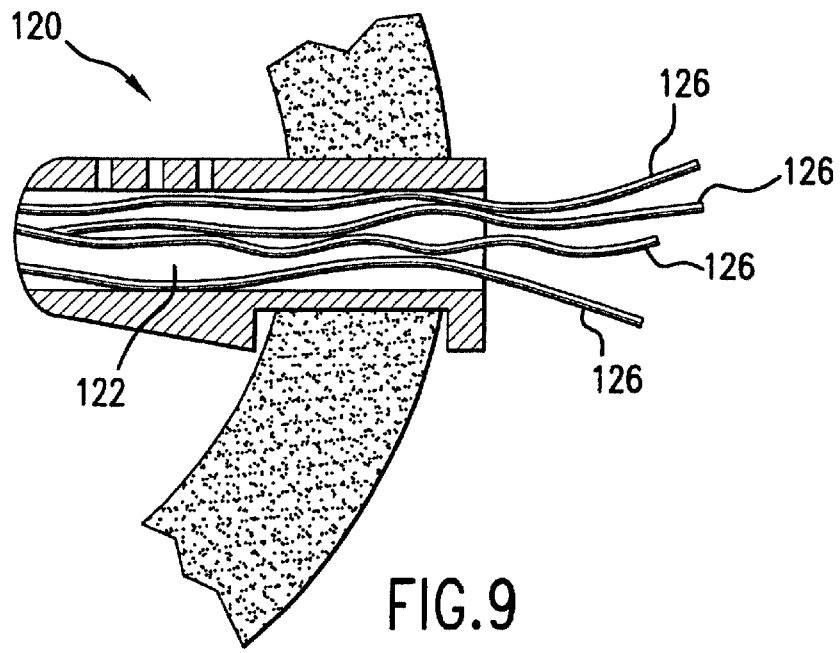
FIG. 9 illustrates an intraocular implant according to the invention with flow controlling strands in the tube passage.
Figure 10:
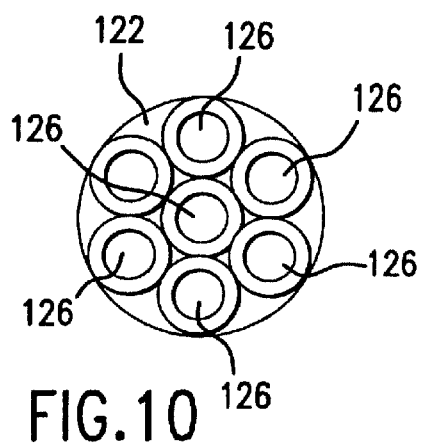
FIG. 10 illustrates an end view of an intraocular implant with flow controlling strands in the tube passage.
Figure 11:
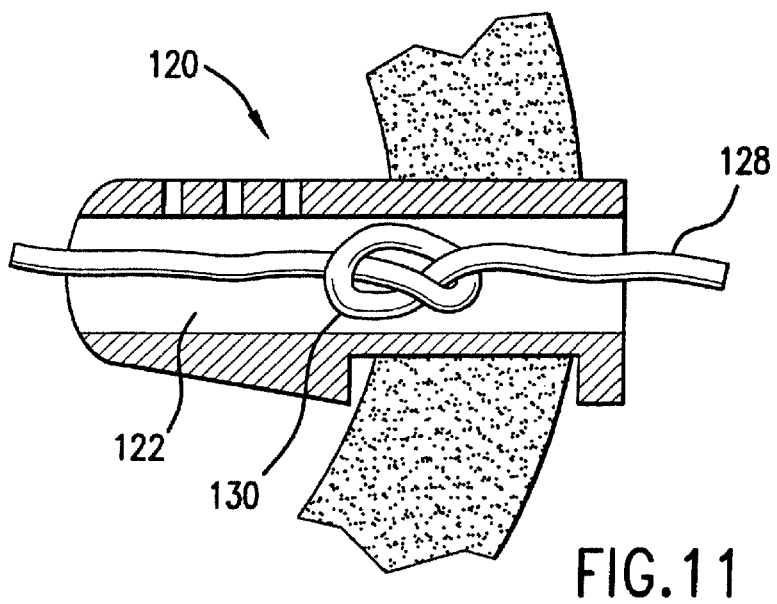
FIG. 11 illustrates an intraocular implant according to the invention with a knotted flow controlling strand in the tube passage.

FIGS. 9 through 11 show alternative mechanisms for partial and/or temporary occlusion of the flow passage. In FIG. 9, the intraocular implant 120 has a number of flow controlling strands 126 in the tube passage 122. The flow controlling strands 126 serve to alter the flow characteristics through the implant, either partially or wholly obstructing flow through the implant. The number and/or size of the strands may be varied as desired, and the strands may be of any suitable material. For example, ordinary sutures, such as polypropylene sutures, may be used.

At a period of time after implantation, one or more of the flow controlling strands 126 may be withdrawn from the implant (or advanced into the implant). Further strands may be withdrawn (or advanced) at later times. In this manner, the obstruction to flow through the implant can be altered, at once or over a period of time, after the implantation procedure has taken place.

It will be appreciated that the ability to withdraw or advance one or more strands over time allows the physician to alter the flow characteristics of the implant in accordance with the needs of the patient. For example, at a certain period of time after the implant has been implanted in a patient's eye, the physician can check the intraocular pressure of the eye and determine whether one or more strands should be withdrawn or advanced to increase or reduce flow through the implant. The patient can be checked periodically, and the strands can be left in place, withdrawn or advanced as appropriate over a period of time.

The ability to withdraw strands is useful in the event the implant should become clogged. In such a case, the physician can withdraw one or more strands in order to restore proper flow through the implant.

FIG. 10 shows an end view of an implant with a plurality of flow controlling strands 126 in the tube passage 122. It will be appreciated that the strands 126 may be arranged within the tube passage 122 in any suitable manner, and the shape and configuration of the strands 126 are not limited to that shown. For example, the strands may have different cross-sections (e.g., oval, semi-circular, irregular, hollow, etc.) and different sizes. The cross-sectional shapes and dimensions may vary along the length of a single strand. Each of the strands in a single implant may have different configurations, e.g., different cross-sectional shapes and/or dimensions. With different strands in the implant, the physician can selectively withdraw (or advance) the appropriate strand or strands in accordance with the desired flow characteristics. For example, if a small increase in flow is desired, a strand with a small cross-section can be withdrawn, and if a larger increase in flow is desired, a strand with a larger cross-section can be withdrawn.

FIG. 11 shows an implant in which a single flow controlling strand 128 having a knot 130 is placed within the tube passage 122. The knot 130 serves to increase the flow obstruction. Alternatively, a plug or other obstruction may be attached to the strand 128, and more than one strand 128 with a knot, plug or other attached obstruction may be used. Similar to the use of strands of different shapes and/or sizes, strands may be used having knots or plugs of different shapes and/or sizes, allowing selective withdrawal or advancement of the appropriate strand or strands in accordance with the desired flow characteristics.

Figure 12:
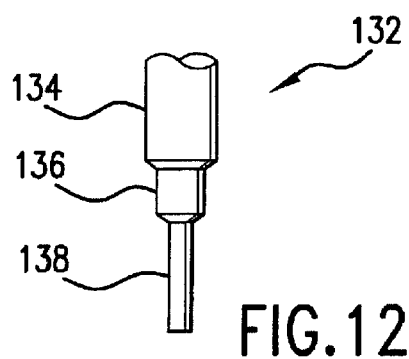
FIG. 12 illustrates an alternative construction of a flow controlling strand.

FIG. 12 shows an alternate construction of a flow controlling strand 132 in which the cross-sectional size of the strand varies along its length. The illustrated strand 132 has three different sections. Section 138 on the end of the strand has the smallest diameter, the adjacent section 136 has a slightly larger diameter, and the remainder 134 of the strand has an even larger diameter. The remainder 134 of the strand may be sized to correspond to the diameter of the tube passage, with the sections 136 and 138 being incrementally smaller. Thus, with a tube passage having a diameter, for example, of 100 microns, the strand may also have a diameter of 100 microns, with incremental steps down to, for example, 20 microns. Of course, other dimensions may be used, and the remainder 134 of the strand need not have the same size as the tube passage. In the initial positioning, the strand 132 is located in the tube passage of the implant with the section 138 near the inlet end and with part of the section 134 located within the tube passage near the outlet end. When it is desired to increase the flow in the implant, the strand 132 may be partially withdrawn such that only section 134 comes out of the tube passage. Thus, the obstruction within the tube passage is decreased, thereby increasing the flow. Later, if desired, the other sections may be successively withdrawn. Alternatively, the strand may be further advanced into the tube passage to further constrict flow.

Variations of the strand shown in FIG. 12 are possible, with the sections being aligned along the strand in any desired pattern. The concept of a single strand which may be partially withdrawn or advanced in successive increments to vary the flow in steps may additionally or alternatively be achieved by using knots or plugs of different shapes and/or sizes along the length of a strand.

A flow controlling strand in accordance with the invention may be completely separate from the implant and inserted into the implant some period of time after implantation, or the strand may be partially in the implant upon implantation, with the option of advancing it further into the implant at a later time.

An implant having withdrawable (and/or advanceable) flow controlling strands may be implanted using a delivery device 30 as shown in FIG. 2A. In such a case, the strands that extend out of the outlet end of the implant may be accommodated in the central bore 36 of the delivery device 30. Alternatively, with a suitably sized opening 40 in the wall of the tube 34 of the delivery device 30, the strands may pass outside of the delivery device 30.

When the implant is implanted in an eye, the flow controlling strands can be oriented to extend under the conjunctiva away from the implant. The strands used may be long enough to extend out of the implant beyond the slit made in the conjunctiva for inserting the implant. In this case, after implanting the implant, the physician can tuck the loose ends of the strands under the conjunctiva to extend away from the slit. When it is desired to withdraw one or more of the strands, a small slit can be made in the conjunctiva near the ends of the strands, and the strands can be pulled through that slit. Because these ends are remote from the implant and the prior slit made in the conjunctiva, the potential trauma to the eye is reduced.

To fix the strands in place and facilitate later access to them, the loose ends may be sutured to the adjacent tissue, e.g., the sclera. This may be done either with additional sutures or with the strands themselves. In the latter case, suturing needles may be attached to the loose ends of the strands to facilitate suturing of the strands after implantation of the implant.

It will be appreciated that various features of the above-described embodiments may be combined as desired. For example, the flow controlling strands may be made of absorbable material, leaving the option of having a physician physically withdraw the strands or allowing them to be absorbed. Additionally or alternatively, plugs or other obstructions secured to the strands may be made of absorbable material. Different strands, plugs or obstructions may be made from materials with different rates of absorption, and/or they may be made from a combination of materials with different rates of absorption.

As will also be appreciated by persons having ordinary skill in the art, the various embodiments of implants, methods of manufacture, delivery devices, and methods for implantation described hereinabove are given by way of example only. Various changes, modifications and variations may be applied to the described embodiments without departing from the scope of the invention, defined by the appended claims.

What is claimed is:

1. An implant in combination with a delivery device for implanting the implant,
    wherein the implant comprises a tube and an outwardly extending retention projection,
    wherein the delivery device comprises a tube having a bore such that the tube of the delivery device has an internal surface substantially bounding the bore and an external surface substantially defining an outer periphery of the tube of the delivery device,
    wherein the bore is dimensioned for accommodating the implant, and
    wherein the delivery device has an opening in the side of the tube allowing the retention projection to project beyond the external surface of the tube of the delivery device.

2. An implant and delivery device according to claim 1, wherein the implant is formed of plastic.

3. An implant and delivery device according to claim 1, wherein the retention projection is located at an inlet end of the implant, and wherein the implant further comprises an outer flange located at an outlet end of the implant.

4. An implant and delivery device according to claim 3, wherein the opening in the side of the tube of the delivery device also allows the outer flange of the implant to project beyond the external surface of the tube of the delivery device.

5. An implant and delivery device according to claim 3, wherein the outer flange of the implant is resilient so that it may be accommodated within the bore of the tube of the delivery device.

6. An implant in combination with a delivery device for implanting the implant,
    wherein the implant comprises a tube having an inlet end and an outlet end and an outwardly extending retention projection,
    wherein the delivery device comprises a tube having a bore such that the tube of the delivery device has an internal surface substantially bounding the bore and an external surface substantially defining an outer periphery of the tube of the delivery device,
    wherein the bore is dimensioned for accommodating the implant,
    wherein the tube of the delivery device has an opening at one end for allowing the implant to exit the bore, and
    wherein the implant is accommodated within the bore with its inlet end closer to the opening than its outlet end so that the inlet end of the implant exits the bore of the delivery device before the outlet end.

7. An implant and delivery device according to claim 6, wherein the implant is formed of plastic.

8. An implant and delivery device according to claim 6, wherein the retention projection is located proximate the inlet end of the implant, and wherein the implant further comprises an outer flange located proximate the outlet end of the implant.

9. An implant and delivery device according to claim 8, wherein the outer flange of the implant is resilient so that it may be accommodated within the bore of the tube of the delivery device.

10. An implant and delivery device according to claim 6, wherein the retention projection of the implant is resilient so that it may be accommodated within the bore of the tube of the delivery device.

11. A delivery device for use in implanting an implant,
    wherein the delivery device comprises a tube having a bore such that the tube of the delivery device has an internal surface substantially bounding the bore and an external surface substantially defining an outer periphery of the tube of the delivery device,
    wherein the bore is dimensioned for accommodating the implant, and
    wherein the delivery device has an opening in the side of the tube allowing a retention projection of the implant to project beyond the external surface of the tube of the delivery device.

12. A delivery device according to claim 11, wherein the opening in the side of the tube of the delivery device also allows an outer flange of the implant to project beyond the external surface of the tube of the delivery device.

13. A method of implanting an implant, comprising the steps of:
    placing the implant in a bore of a delivery device, said placing step including allowing a retention projection of the implant to project beyond an external surface of a tube of the delivery device;

inserting the delivery device with the implant placed in the delivery device through tissue into which the implant is to be implanted; and withdrawing the delivery device, leaving the implant implanted in the tissue.

14. A method of implanting an implant, comprising the steps of:

placing the implant in a bore of a delivery device, said placing step including positioning the implant so that the implant is accommodated within the bore with an inlet end of the implant closer to an opening in the delivery device than an outlet end of the implant;

inserting the delivery device with the implant placed in the delivery device through tissue into which the implant is to be implanted; and withdrawing the delivery device, leaving the implant implanted in the tissue.

* * * * *